(12) United States Patent
Mohan et al.

(10) Patent No.: US 9,515,618 B2
(45) Date of Patent: *Dec. 6, 2016

(54) FEMTOWATT NON-VACUUM TUBE DETECTOR ASSEMBLY

(71) Applicant: Theranos, Inc., Palo Alto, CA (US)

(72) Inventors: Karan Mohan, Palo Alto, CA (US); Marcelo Martinez, Palo Alto, CA (US)

(73) Assignee: Theranos, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/849,264

(22) Filed: Sep. 9, 2015

(65) Prior Publication Data

US 2016/0072453 A1    Mar. 10, 2016

Related U.S. Application Data

(63) Continuation of application No. PCT/US2014/030823, filed on Mar. 17, 2014.

(60) Provisional application No. 61/801,996, filed on Mar. 15, 2013.

(51) Int. Cl.
| | |
|---|---|
| *H03F 3/02* | (2006.01) |
| *H03F 3/08* | (2006.01) |
| *H01L 31/02* | (2006.01) |
| *G01N 15/14* | (2006.01) |
| *H03M 1/06* | (2006.01) |
| *G01N 21/64* | (2006.01) |
| *G01N 15/06* | (2006.01) |
| *G01N 15/10* | (2006.01) |

(52) U.S. Cl.
CPC ............ *H03F 3/08* (2013.01); *G01N 15/1434* (2013.01); *H01L 31/02019* (2013.01); *H03M 1/0607* (2013.01); *G01N 21/645* (2013.01); *G01N 2015/0693* (2013.01); *G01N 2015/1006* (2013.01)

(58) Field of Classification Search
CPC ............... H03F 3/02; H03F 3/45; H04B 10/00
USPC ............ 250/214 R, 214 VT, 214 A, 214 LA, 250/214 DC, 208.2; 398/202, 208, 209
See application file for complete search history.

(56) References Cited

U.S. PATENT DOCUMENTS

| | | |
|---|---|---|
| 5,070,332 A | 12/1991 | Kaller et al. |
| 6,344,651 B1 | 2/2002 | Woolaway et al. |
| 7,005,646 B1 | 2/2006 | Jordanov et al. |
| 7,250,893 B2 * | 7/2007 | Todoroff ................. H03M 1/50 250/208.1 |
| 7,605,357 B2 | 10/2009 | Fathimulla et al. |
| 8,948,610 B2 * | 2/2015 | Azadeh ................ H04B 10/695 375/317 |
| 2002/0154364 A1 | 10/2002 | Green et al. |
| 2005/0116778 A1 | 6/2005 | Braier et al. |
| 2010/0172656 A1 | 7/2010 | Saitou et al. |
| 2011/0293293 A1 | 12/2011 | Sugimoto |
| 2011/0318015 A1 | 12/2011 | Sugimoto |
| 2012/0039615 A1 * | 2/2012 | Cho ..................... H04B 10/801 398/142 |

FOREIGN PATENT DOCUMENTS

WO    2014145963 A2    9/2014

OTHER PUBLICATIONS

International Search Report dated May 15, 2016 for PCT/US2014/030823.

* cited by examiner

*Primary Examiner* — Kevin Pyo

(57) ABSTRACT

In one embodiment, a femtowatt sensitivity optical detector is provided using one or more photodiodes, intended as a replacement for the photomultiplier based photon counting unit.

20 Claims, 7 Drawing Sheets

FEMTOWATT NON-VACUUM TUBE DETECTOR ASSEMBLY

BACKGROUND

Photomultiplier tubes (PMTs for short), members of the class of vacuum tubes, and more specifically vacuum phototubes, are extremely sensitive detectors of light in the ultraviolet, visible, and near-infrared ranges of the electromagnetic spectrum. Unfortunately, current techniques of manufacturing PMTs is a tedious and costly process. Many manufacturers have opted to stop production of PMTs due these challenges. In addition to manufacturing issues, although highly sensitive, PMTs also saturate easily when too much light reaches it.

SUMMARY

At least some of the disadvantages associated with the prior art are overcome by at least some embodiments of the devices and methods described herein.

In one embodiment, a femtowatt sensitivity optical detector is provided using one or more photodiodes, intended as a replacement for the photomultiplier based photon counting unit.

In one embodiment, the system is comprised of four main components: Multiple photodiodes, which act as optical transducers by producing an electrical signal in the form of a current proportional to the detected optical power (number of photons). 1) Analog amplification system, composed of a high gain transimpedance amplifier (TIA) and buffer on each photodiode, followed by a fully differential amplifier to combine the outputs of the multiple TIAs. 2) Digital acquisition system, composed of an analog to digital converter (ADC), followed by an programmable processor, which is linked to the central processor as well as on board memory. The programmable processor implements the data acquisition algorithm such as an average or other algorithm. 3) Multiple digital to analog converters (DACs) on the programmable processor are used to provide feedback control—one for offset adjustment in the differential amplifier, and one to the set the reference level of the ADC. 4) Mechanical housing module, in which the electronics is contained.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference. However, in the event of a conflict between the content of the present express disclosure and the content of a document incorporated by reference herein, the content of the present express disclosure controls.

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013-14 Theranos, Inc.

DESCRIPTION OF THE SPECIFIC EMBODIMENTS

Figure 1:
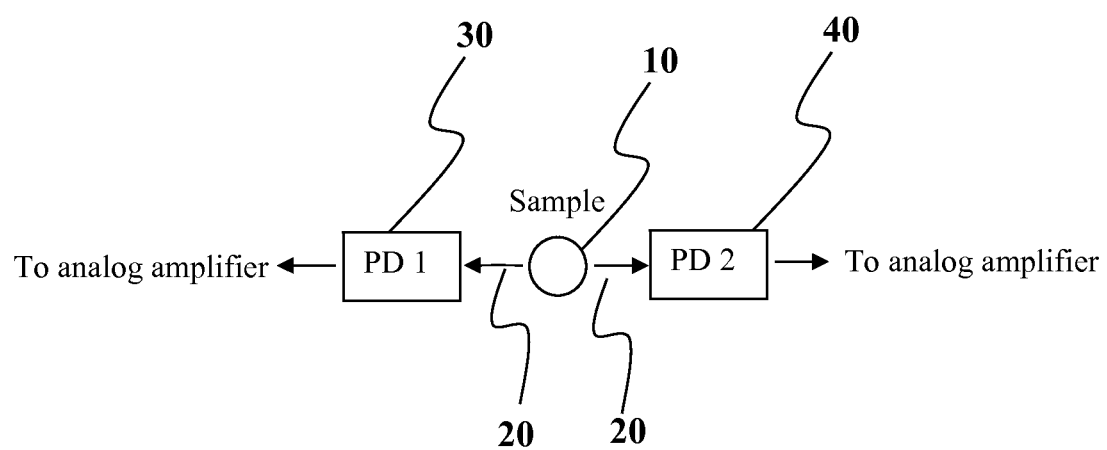
FIGS. 1 to 3 show schematics of systems according to embodiments described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

Referring now to FIG. 1, one non-limiting example of photodiode (PD) placement is shown, relative to the chemiluminescent sample 10. The arrows 20 indicate the direction of emitted of photons. In one non-limiting example, the photodiodes 30 and 40 are operated in zero bias mode—this ensures that the only source of noise is thermal noise. They are situated as close as possible to the chemiluminescent sample, allowing the collection of as much emitted light as possible. In addition, pairs of photodiodes are on equal and opposite sides of the sample, ensuring a symmetric collection of light. FIG. 1 illustrates the placement of two photodiodes, and the design is readily extended to multiple photodiodes.

In one non-limiting example, the output of each photodiode is a current proportional to the amount of light incident. For a sample whose emission is constant in time, this generates a DC current. By way of example and not limitation, silicon photodiodes with the following properties are used for the photodiodes 30 and 40: Large active area, Low noise equivalent power, High sensitivity (in % quantum efficiency or responsivity A/W).

Analog Amplification System

Figure 2:
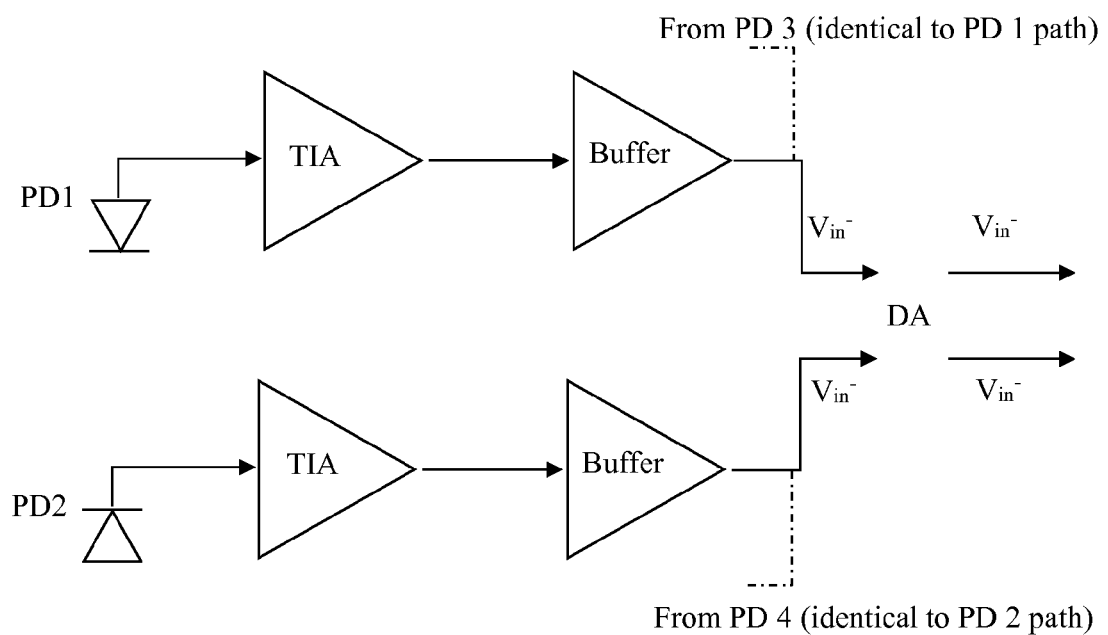

Referring now to FIG. 2, an analog amplification system suitable to be coupled to the photodiodes 30 and/40 will now be described. By way of example and not limitation, an analog amplifier system in this embodiment is comprised of three stages as shown in FIG. 2. The dotted lines suggest the possible extension of the amplifier to include multiple photodiodes.

In this non-limiting example, one stage is a high gain transimpedance amplifier (TIA), with gain of $10^{10}$ V/A or greater. Each photodiode in the system is connected to a TIA, whose input is the DC signal current from the photodiode. The output of the TIA is a DC voltage.

In this non-limiting example, one stage is a buffer stage following the transimpedance amplifier, to isolate the first stage from later stages.

In this non-limiting example, one stage is a differential amplifier (DA) stage, which combines the outputs from multiple transimpedance amplifiers. The differential amplifier is comprised of a positive and negative output, such that $(V_{out}^{+}-V_{out}^{-})=A(V_{in}^{+}-V_{in}^{-})$, where A is the gain. This gain is adjustable and controlled by the digital acquisition system, so as to maximize the output range for the particular sample under test.

The analog amplification system for a pair of photodiodes is illustrated in FIG. 2. Single or multiple pairs of photodiodes are connected in opposite directions. Thus, the optical signal component of $V_{out}^{-}$ is always 180 degrees out of phase with that of $V_{out}^{+}$, resulting in up to twice the signal when the difference $(V_{out}^{+}-V_{out}^{-})$ is measured for two photodiodes. All other common signals (60 Hz pickup, DC drift, etc) are in phase along the different paths, and therefore cancel out when the difference is measured. Noise adds in quadrature, giving 1.4 times the noise on each path, in the case of two photodiodes.

Furthermore, each stage of the analog amplifier may optionally contain a low pass filter for additional noise reduction.

Digital Acquisition System

Figure 3:
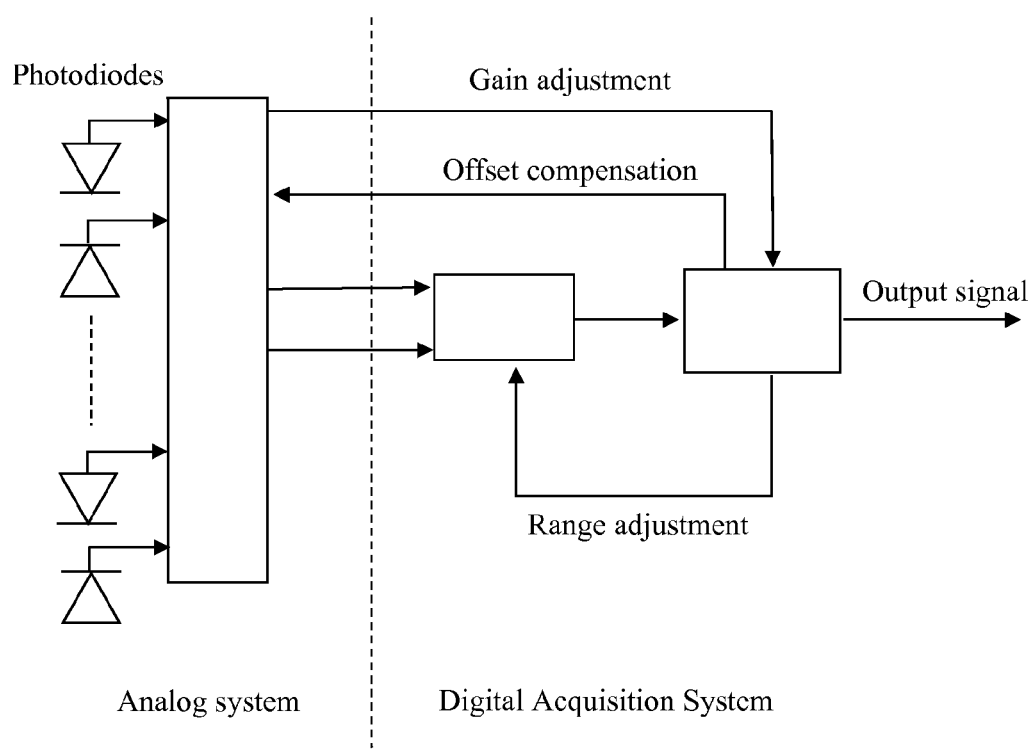

Referring now to the embodiment of FIG. 3, one non-limiting example of a complete photodiode detector system will now be described. The schematic of FIG. 3 shows the components and connections between the analog and digital system. The digital acquisition system, in relation to the analog system is illustrated in FIG. 3. In this non-limiting example, the outputs of the analog amplifier system ($V_{out}^{+}$ and $V_{out}^{-}$) are fed into the digital acquisition system, comprised of:

A differential analog-to-digital converter (ADC), with high sampling rate (>1MSPS) and high precision (>16 bits). The output of the ADC is a digital signal representing the difference ($V_{out}^{+}-V_{out}^{-}$).

An digital processor, which collects the data from the ADC over a set time interval, and implements an algorithm whose output is digitally processed. By way of non-limiting example, the sample may be processed by performing one or more the following digital signal processing on the data collected: smoothing data processing, additive smoothing, Savitzky-Golay smoothing, moving average smoothing, local regression smoothing, Butterworth filtering, Kalman filtering, Kernel smoothing, Laplacian smoothing, Stretched grid method smoothing, low-pass filtering, recursive filter median, long time average, any single or multiple combination of the foregoing, or other digital processing techniques to remove noise. This latter process measures the DC level of the signal of interest, and further reduces the noise level. A digital processor such as that available from ARM, Texas Instruments, or the like can configured for use herein.

The digital processor may also contain digital-to-analog converters (DAC), one of which is used to compensate any DC level offset of the DA output (due to natural processes such as amplifier drift and leakage currents). A second DAC is used to adjust the range of the ADC. The ARM also controls the gain of the DA stage. These three feedback controls maximize the dynamic range and measurement precision for a particular sample being tested.

Finally, the digital processor optionally converts the measured DC signal to an equivalent photon count.

Mechanical Housing Module

The mechanical housing in which the above electronics are contained is designed with the following requirements:

Multiple circuits (and sub-circuits) are isolated from each other by grounded surfaces, to prevent parasitic capacitive and inductive cross-talk.

The complete system is isolated from the environment, by ensuring that the housing is made of a grounded, conductive material (e.g. aluminum). This minimizes pickup from the environment, such as 60 Hz and other electromagnetic interference.

Control System

One embodiment of the analog capture system in FIG. 2 that collect signal from the photodiodes has a differential amplifier mode. In this non-limiting example, there is a front-end photodiode circuit which provides an analog front end. To detect photons at low light levels (say 1000 photons per second) versus regular light (billons of photons). The signal is very small that is then amplified to be above the noise level. A PMT has an in-built gain system that allows it amplify signal without noise. It is a single photon counter, but it is hard to manufacture and saturates easily.

In one embodiment, a femtowatt level sensitivity optical detector is provided using at least one photodiode. It can be configured to provide PMT-level sensitivity. In one embodiment, at least two photodiode detectors are used to detect signal from the sample as seen in FIG. 1. A control circuit is used to combine the signal in a differential manner. One manner is to add the signals to get a total signal out. The other way is to use a differential mode where one signal is a positive signal and the other is a negative signal and then instead of adding, they are put through a subtraction to substrate the negative signal. Because noise does not care if it is positive or negative, the present embodiment can use a subtraction function when signals are combined to minus out the noise (whereas using addition would not). The ability to have two, four, six, or other number of combination can be combined at the control. Many photodiodes can be added the embodiment of FIG. 1 and be supported by analog systems of FIG. 2 for signal capture. This can collect more light than the PMT and in theory can go to more sensitive chemistries since more light is being collected.

Embodiments herein can also correlate its output (in volts) to that of the with PMT sample device (output in photon counts). Photodiode detects 10 times more light, but it can be configured to correlate to PMT type output.

It should be understood that a PMT will saturate at 500000 photons per half second. (200 to 200 k) The photodiode can measure 2 million per half second. This provides much more tolerance for situations.

Figure 4:
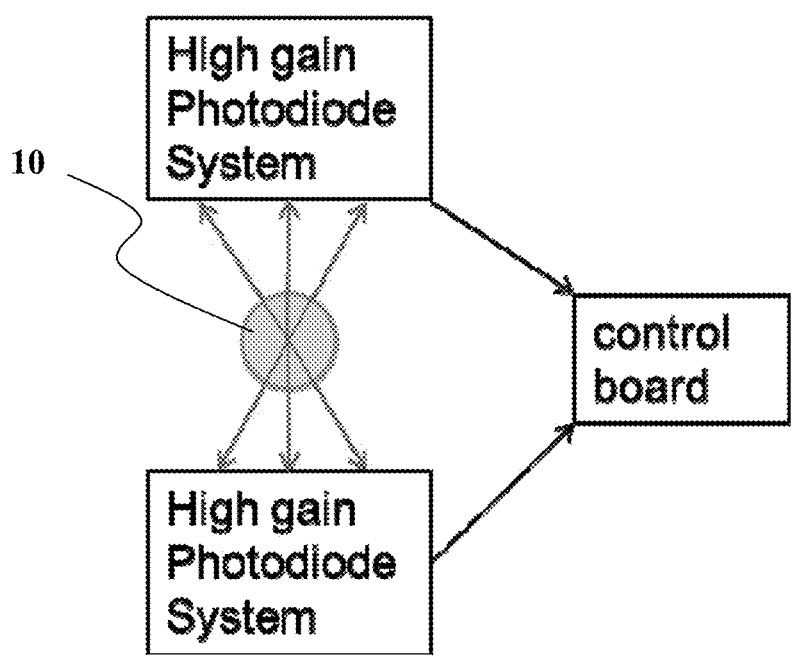
FIGS. 4 to 5 show schematics of systems according to embodiments described herein.

As seen in FIG. 4, one embodiment of the system uses a plurality of high gain photodiodes to collect light from multiple locations around the sample and then direct the detected signal to the control board that has an analog front end similar to that in FIG. 2 to prepare the analog signal which is then processed digitally in the digital portion shown in FIG. 3. Some embodiment can envision a sphere or other configuration of many multiple photodiodes position to capture light from the sample in many directions.

As seen in FIG. 4, one embodiment of the control board can combine photodiode signals as a sum, or differentially. In both cases, the noise adds in quadrature, e.g. if two photodiodes are used, with noises $N_1$ and $N_2$, then total noise is:

$$N=\sqrt{N_1^2+N_2^2}$$

Signals on the other hand, add linearly; so the total signal is $S_1+S_2$ in the case of two photodiodes. Thus signal to noise always improves. Differential mode allows removal of common unwanted signals; some may have the photodiodes have alternating polarity (cathode grounded, anode grounded).

Reflector System

It should be understood that electronics generally adds noise. Thus adding even more photodiodes, while increase light capture, can also detrimentally increase noise levels. One option is to minimize electronics but increase the amount of light collected at any one sensor. One option is to move photodiode closer to sample. Some may combine both of the foregoing.

Figure 5:
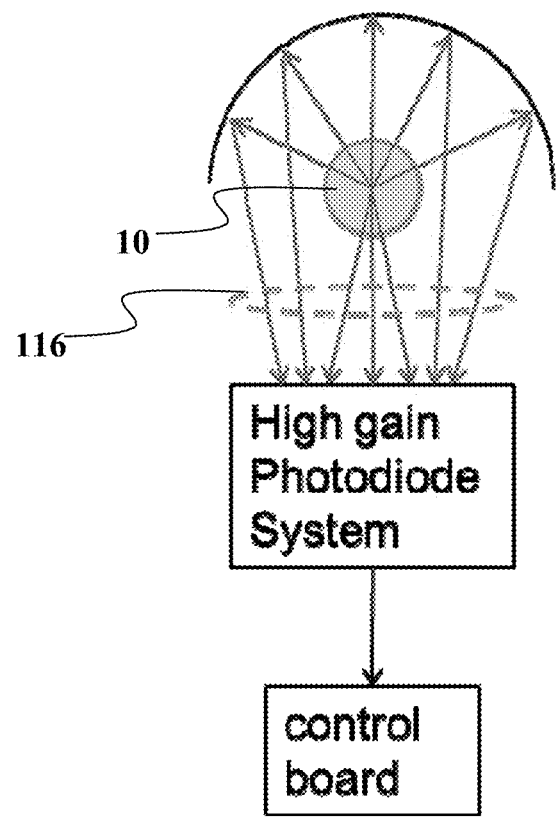

As seen in FIG. 5, a still further embodiment of a non-vacuum tube femotwatt detector will now be described. In this embodiment, the reflector is custom designed to increase light capture. Some embodiments may have one or more opening is there for the sample tip to be lowered into the area of the reflector. Some light will pass through the sample (and it does not excite the sample). This could be an aspherical reflector. Reflection can be aluminum or other reflective material for all wavelength reflection without absorbance.

FIG. 5 shows that this embodiment captures light that would otherwise not reach the high gain photodiode and redirects it toward the one or more photodiodes. Some embodiments may use a hemispherical reflector, a dish-shaped detector, a curved detector, or the like. Optional lens 116 may be positioned to collect emitted and reflected light.

It should be understood that irradiance is smaller if power is spreadout over a larger area. There may be some benefit to lens 116 to focus light to exceed a minimum turn-on threshold or reach a threshold irradiance for certain types of sensors. Optionally, for a CCD sensor, light is spread over too many pixels. Then if it does not overcome light per pixel, it may help for turn-on. CCD type application may be useful for determining how much light is coming from each location in the sample. In one embodiment, this turns this system into an imaging device through the use of CCDs.

Figure 6:
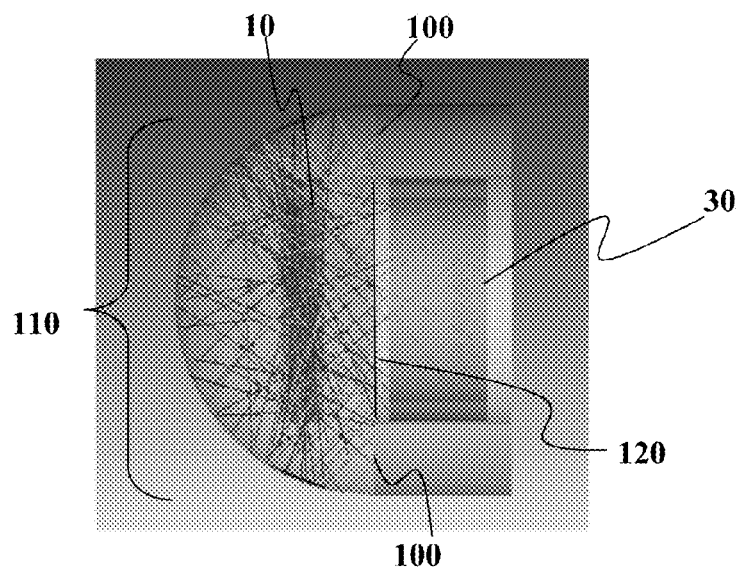
FIG. 6 shows a side view of one assembly herein using a reflector according to at least one embodiment described herein.
Figure 7:
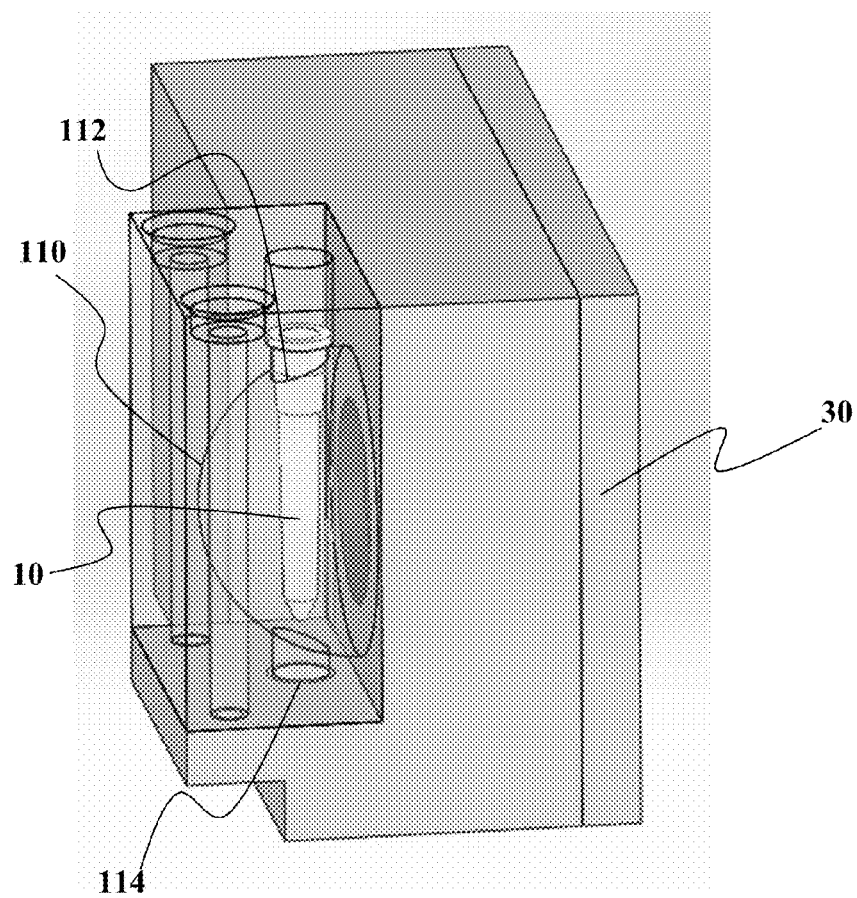
FIG. 7 shows a perspective view of one assembly herein using a reflector according to at least one embodiment described herein.

FIG. 6 shows the wall surfaces 100 that are around the photodiode but perhaps not part of the reflector 110 may also be configured to be reflective. FIG. 6 also shows that for various reasons, some embodiment may have a transparent cover 120 over the photodiode. In one embodiment, the transparent cover 120 is electrically insulating. In one embodiment, the transparent cover 120 is electrically conductive. Optionally, one could switch off the photodiode while the sample is moving into position. Once the sample is in place, then the photodiode switches on to measure. This has the added advantage that since we are essentially resetting the device during every read, the electronics is not allowed to drift over time or be affected by parasitic light sources. Although only one photodiode is shown in FIGS. 5 and 6, it should be understood that could place multiple photodiodes to maximize collection efficiency FIG. 7 shows a perspective view of one embodiment of the system with a reflector 110. FIG. 7 shows that in this non-limiting example, there may be an opening 112 that allows for a sample to be lowered into position for analysis. A second opening 114 can also be positioned there to allow for sample fluid to drip out and not collect inside the reflector 110. Optionally, there can be lid that covers the opening 112 and/or 114 to increase the amount of light capture. There can also be embodiments where the entire reflector 110 comes away to allow for sample loading. Optionally, a holder can be mounted in the reflector 110 so that the sample handling system is not holding the sample 10 during detection.

Dual Fluoro-Luminometer

Figure 8:
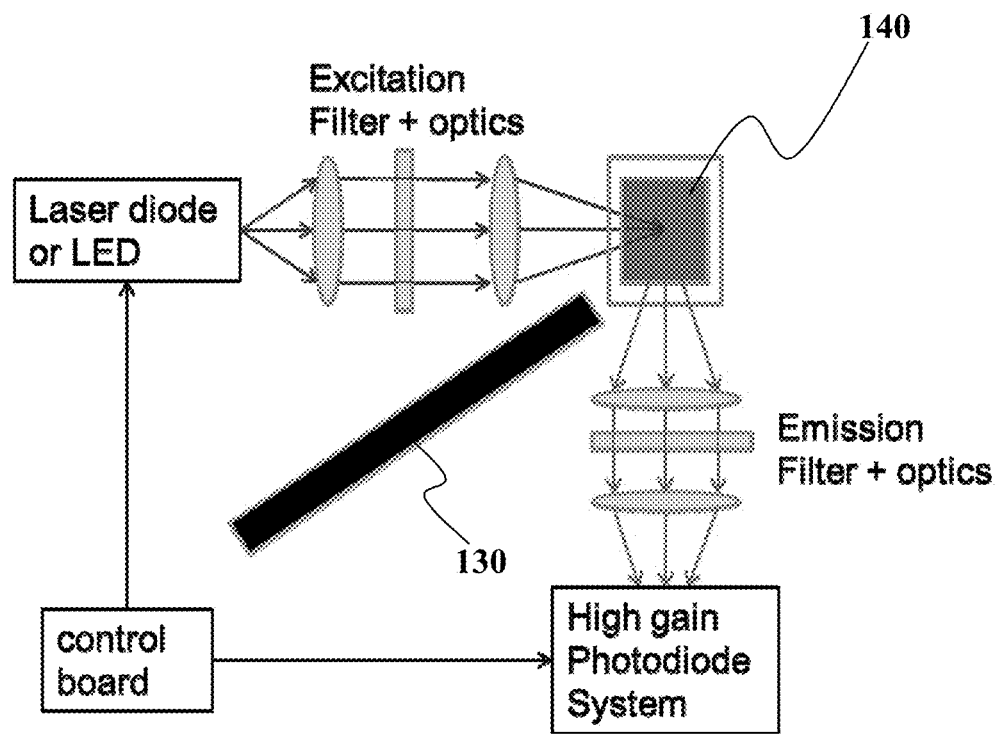
FIG. 8 show a schematic of an assembly according to embodiments described herein.

Referring now to FIG. 8, it should be understood that some embodiments may combine the system to have both fluorometer and a luminometer functions. By way of non-limiting example, an LED or laser can be used to excite the sample. Some embodiments add a light excitation source and thus does not use a reflector. Optical barrier 130 is used to reduce bleed-through. By way of example and not limitation, a cube shaped vessel 140 may be used to reduce scatter/bleed through, or a tip vessel with a truncated cone shape.

It should be understood that one could have more than one control board to read more than one device. The control board above in FIG. 8 that has feature set forth in FIGS. 2 and 3 is designed to have the ability to read multiple photodiodes in different modes. When run simultaneously, the control board can combine signals from different photodiodes. This can be done in summing or differential mode as described above. When run individually, the control board can read signals from selected photodiodes. Optionally, in a combination of these two cases, where we can selectively read some of the photodiodes and combine their signals— e.g. one can read 3 out of 4 photodiodes simultaneously, and ignore the 4th. This flexibility allows the system control board to control both the fluorometer and luminometer with a single control board.

The fluorometer can be used to perform dynamic dilution measurements for cytometry—this is currently done on the spectrometer, but the fluorometer would offer a more sensitive option. There is also the potential option of doing additional functions of cytometry, thought not quite all the same capabilities as the cytometer.

Due to the high sensitivity of the electronics to EMI, the all electronics need to be placed in a metal housing, which is grounded. Furthermore, the thickness of the housing's walls are designed such that both low (60 Hz) to high (kHz to MHz) frequencies are blocked.

System

In embodiments, devices comprising a femtowatt sensitivity photodiode assembly, and systems and methods comprising or using such devices, may comprise a controller. In embodiments, a controller may comprise a processor. In embodiments, a controller may be connected to, and may control the operation of, components of a device; such components are typically disposed within a housing of the device. In embodiments, a controller may control the operation of a femtowatt sensitivity photodiode assembly. In embodiments, a controller may control the operation of a sample handling system. In embodiments, a controller may control the operation of a detector. In embodiments, a controller may control the operation of any component or unit of the device. Other components may include, for example, a camera, a chemistry assay unit, a nucleic acid assay unit, a heating unit, a communication unit, a protein chemistry unit, or other component or unit. In embodiments, a controller may control the operation of one or more components of a device according to a protocol. In embodiments, a protocol by which a controller controls the operation of any one or more component or unit of a device may be preprogrammed, e.g., may be resident on the device. In embodiments, a protocol by which a controller controls the operation of any one or more component or unit of a device may be obtained from another device, or from a user, or from a laboratory, or from a network, or from the cloud. In embodiments, a protocol by which a controller controls the operation of any one or more component or unit of a device may be updated, or may be updatable, according to information or instructions from another device, or from a user, or from a laboratory, or from a network, or from the cloud. In embodiments, a device may receive information, or instructions, or updates, or protocols, via a user interface. In embodiments, a device may receive information, or instructions, or updates, or protocols, via a communication assembly. The system can, in one embodiment, have optical detectors at four levels of sensitivity with the least sensitive is the spectrometer. Next is cytometer. Nucleic acid is more sensitive than cytometer. Then the PMT is most sensitive (3 to 4 orders of magnitude of sensitivity higher than the next most sensitive sensor).

In embodiments, devices comprising a femtowatt sensitivity photodiode assembly, and systems and methods comprising or using such devices, may comprise a display effective to provide a user with information regarding the operation of the device, information regarding the progress of an assay performed by the device, or information regarding the results of an assay performed by the device. In embodiments, a display may comprise a visual display, or may comprise a printed display, or may comprise an audio signal, which may include an audio signal understandable as speech by a user, or may comprise any combination or all of such displays. In embodiments, a display may comprise a user interface. In embodiments in which a display comprises a user interface, a device may receive, e.g., information, commands, protocols, or other input.

In embodiments, devices comprising a femtowatt sensitivity photodiode assembly, and systems and methods comprising or using such devices, may comprise a communication assembly effective to communicate with one or more of a user, another device, a laboratory, a network, the cloud, or other communication target. In embodiments, a communication assembly may provide a communication target with information regarding the operation of the device, information regarding the progress of an assay performed by the device, or information regarding the results of an assay performed by the device. In embodiments, a communication assembly may be configured to allow a device to receive, e.g., information, commands, protocols, or other input from an outside source, such as, e.g., a user, another device, a laboratory, a network, the cloud, or other communication source.

As used herein the terms "sample handling system", "fluid handling system" and grammatical equivalents refer to systems configured to obtain, transport, and deliver fluids. In embodiments disclosed herein, such systems comprise pipettes, nozzles, pipette tips, mechanical components configured to move a pipette, a nozzle, or a pipette tip to a desired location. Such a desired location is typically within a housing of a device. In embodiments, a pipette tip may be mounted on a nozzle; in embodiments, a pipette tip may be removably mounted on a nozzle, effective that a nozzle may engage and mount a first pipette tip, use the first pipette tip, discard the first pipette tip, and then engage and mount a second pipette tip. Such systems comprise means for aspirating liquid into a pipette tip. Such systems comprise means for dispensing liquid from a pipette tip. In embodiments of such systems, a pipette and nozzle may engage and mount an element other than a pipette tip; for example, in embodiments disclosed herein, a pipette and nozzle may engage and mate with a mating socket of a vessel (see, e.g., FIGS. 10 and 11). In embodiments, a pipette and nozzle mated with a mating socket of a vessel may be used to transport the vessel to a desired location within a device. In embodiments, a pipette and nozzle mated with a mating socket of a vessel may be used to apply force to a vessel (see, e.g., FIG. 11 for a configuration where such application of force may be useful).

The methods disclosed herein can be readily incorporated into and used in device for processing a sample, or a system for processing a sample, which may be an automated assay device, or may be an automated assay system. Such assay devices and assay systems may comprise devices and systems disclosed, for example, in U.S. Pat. No. 8,088,593; U.S. Pat. No. 8,380,541; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties.

Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be a sample processing device. A device may be a sample processing device. A sample processing device may be configured to facilitate collection of a sample, prepare a sample for a clinical test, or effect a chemical reaction with one or more reagents or other chemical or physical processing, as disclosed herein. A sample processing device may be configured to obtain data from a sample. A sample processing device may be configured to transmit data obtained from a sample. A sample processing device may be configured to analyze data from a sample. A sample processing device may be configured to communicate with another device, or a laboratory, or an individual affiliated with a laboratory, to analyze data obtained from a sample.

A sample processing device may be configured to be placed in or on a subject. A sample processing device may be configured to accept a sample from a subject, either directly or indirectly. A sample may be, for example, a biological sample, e.g., of blood, urine, sputum, material obtained from a nasal swab, a throat swab, a cheek swab, or other sample, (e.g., a sample obtained from a fingerstick, or from venipuncture, or an arterial biological sample, e.g., of blood, urine, sputum, material obtained from a nasal swab, a throat swab, a cheek swab, or other sample,), a urine sample, a biopsy sample, a tissue slice, stool sample, or other biological sample; a water sample, a soil sample, a food sample, an air sample; or other sample. A biological sample, e.g., of blood, urine, sputum, material obtained from a nasal swab, a throat swab, a cheek swab, or other sample, may comprise, e.g., whole blood, plasma, or serum. A sample processing device may receive a sample from the subject through a housing of the device. The sample collection may occur at a sample collection site, or elsewhere. The sample may be provided to the device at a sample collection site.

In some embodiments, a sample processing device may be configured to accept or hold a cartridge. In some embodiments, a sample processing device may comprise a cartridge. The cartridge may be removable from the sample processing device. In some embodiments, a sample may be provided to the cartridge of the sample processing device. Alternatively, a sample may be provided to another portion of a sample processing device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, a sample processing device, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as a sample processing device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the sample processing device. The sample, reagent, or aliquot thereof can be deposited at a location on or within the sample processing device. Sample and reagent, or multiple reagents, may be mixed using a sample handling system in a similar manner. One or more components of the cartridge may be transferred in an automated fashion to other portions of the sample processing device, and vice versa.

A device, such as a sample processing device, may have a fluid handling system (also termed herein a sample handling system). A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

A fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

A sample processing device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. A sample processing device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a biological sample, e.g., of blood, urine, sputum, material obtained from a nasal swab, a throat swab, a cheek swab, or other sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

A sample processing device may be configured to run one or more assay on a sample, and to obtain data from the sample. An assay may include one or more physical or chemical treatments, and may include running one or more chemical or physical reactions. A sample processing device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

A sample processing device may be configured to perform a plurality of assays on a sample. For example, a sample processing device may be configured to detect, or to identify, or to measure pathogen-identifying material in a sample. In embodiments, a sample processing device may be configured to perform a plurality of assays on a single sample. In embodiments, a sample processing device may be configured to perform a plurality of assays on a single biological sample, where the biological sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. A sample processing device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

A sample processing device may be configured to detect one or more signals relating to the sample. A sample processing device may be configured to identify one or more properties of the sample. For instance, the sample processing device may be configured to detect the presence or concentration of one analyte or a plurality of analytes or a disease condition in the sample (e.g., in or through a bodily fluid, secretion, tissue, or other sample). Alternatively, the sample processing device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, a sample processing device may be configured to transmit data obtained from a sample. In embodiments, a sample processing device may be configured to communicate over a network. A sample processing device may include a communication assembly that may interface with the network. A sample processing device may be connected to the network via a wired connection or wirelessly. The network may be a local area network (LAN) or a wide area network (WAN) such as the Internet. In some embodiments, the network may be a personal area network. The network may include the cloud. The sample processing device may be connected to the network without requiring an intermediary device, or an intermediary device may be required to connect a sample processing device to a network. A sample processing device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

A sample processing device may provide data regarding a sample to, e.g., a health care professional, a health care professional location, such as a laboratory, or an affiliate thereof. One or more of a laboratory, health care professional, or subject may have a network device able to receive or access data provided by the sample processing device. A sample processing device may be configured to provide data regarding a sample to a database. A sample processing device may be configured to provide data regarding a sample to an electronic medical records system, to a laboratory information system, to a laboratory automation system, or other system or software. A sample processing device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by a sample processing device, or analysis of such data, or reports, may be provided to a database, an electronic medical records system, to a laboratory information system, to a laboratory automation system, or other system or software While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that different shaped reflectors can be used. Some may have cross-sectional shapes such as but not limited to elliptical, triangular, quadrilateral (e.g., square, rectangular, trapezoidal, parallelogram), pentagonal, hexagonal, heptagonal, octagonal, square, circular, star, other two dimensional patterns, or single or multiple combinations of the foregoing. It should also be understood that the reflectors may be configured to be in certain three dimensional configurations such as but not limited to tubular, cylindrical, disc, pyramid, mesa, or the like can also be adapted for use herein. Although the examples herein are described in the context of photodiodes, it should be understood that other solid-state or semiconductor (non-vacuum tube) detectors can also be adapted for use herein.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc. . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes: U.S. Pat. No. 8,088,593; U.S. Pat. No. 8,380,541; U.S. patent application Ser. No. 13/769,798, filed Feb. 18, 2013; U.S. patent application Ser. No. 13/769,779, filed Feb. 18, 2013; U.S. Pat. App. Ser. No. 61/766,113 filed Feb. 18, 2013, U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, U.S. Patent Application Ser. No. 61/786,351 filed Mar. 15, 2013, U.S. Patent Application Ser. No. 61/697,797 filed Sep. 6, 2012, U.S. Patent Application Ser. No. 61/801,996 filed Mar. 15, 2013, and U.S. Patent Application Ser. No. 61/733,886 filed Dec. 5, 2012, the disclosures of which patents and patent applications are all hereby incorporated by reference in their entireties for all purposes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

What is claimed is:
1. A device comprising:
a plurality of photodiodes;
an analog amplification system comprising at least a high gain transimpedance amplifier (TIA) and at least a buffer on each of said photodiodes, followed by a fully differential amplifier to combine outputs of multiple TIAs;

a digital acquisition system comprising at least one analog-to-digital converter (ADC), followed by a programmable processor, which is linked to a central processor as well as on-board memory; and at least one shaped reflector to direct light to at least one of said photodetectors, wherein the shaped reflector comprises at least one opening sized and positioned to allow a sample vessel to be placed at a desired location in a cavity defined at least in part by the shaped reflector.

2. The device of claim 1 further comprising a mechanical housing module of the analog amplification system are contained.

3. The device of claim 1 wherein the programmable processor implements the data acquisition algorithm.

4. The device of claim 1 further comprising multiple digital-to-analog converters (DACs) on the programmable processor configured to provide feedback control.

5. The device of claim 4 wherein one of said DACs is configured for offset adjustment in the differential amplifier, and one of said DACs is set the reference level of the ADC.

6. The device of claim 1 wherein the shaped reflector has a semi-hemispherical shape.

7. The device of claim 4, wherein one of the DACS is configured for offset adjustment in the differential amplifier.

8. The device of claim 4, wherein one of the DACS is configured to set a reference level of the ADC.

9. The device of claim 5, wherein one of the DACS is configured for offset adjustment in the differential amplifier.

10. The device of claim 5, wherein one of the DACS is configured to set a reference level of the ADC.

11. The device of claim 3, wherein data acquisition algorithm uses the following digital signal processing: smoothing data processing.

12. The device of claim 3, wherein data acquisition algorithm uses the following digital signal processing: Savitzky-Golay smoothing.

13. The device of claim 3, wherein data acquisition algorithm uses the following digital signal processing: moving average smoothing.

14. The device of claim 3, wherein data acquisition algorithm uses the following digital signal processing: local regression smoothing.

15. The device of claim 3, wherein data acquisition algorithm uses the following digital signal processing: recursive filter median.

16. The device of claim 3, wherein data acquisition algorithm uses the following digital signal processing: long time average.

17. The device of claim 3, wherein data acquisition algorithm uses the following digital signal processing: Butterworth filtering.

18. The device of claim 3, wherein data acquisition algorithm uses the following digital signal processing: Kalman filtering.

19. The device of claim 3, wherein data acquisition algorithm uses the following digital signal processing: Kernel smoothing.

20. The device of claim 3, wherein data acquisition algorithm uses the following digital signal processing: Laplacian smoothing.

* * * * *